United States Patent [19]

Doi

[11] Patent Number: 4,997,909

[45] Date of Patent: Mar. 5, 1991

[54] RANDOM COPOLYMER COMPRISING D-(−)-3-HYDROXYBUTYRATE UNITS AND D-(−)-3-HYDROXYVALERATE, AND PROCESS FOR PRODUCTION THEREOF

[75] Inventor: Yoshiharu Doi, Yokohama, Japan

[73] Assignee: Mitsubishi Gas Chemical Company, Inc., Tokyo, Japan

[21] Appl. No.: 532,167

[22] Filed: Jun. 5, 1990

Related U.S. Application Data

[63] Continuation of Ser. No. 183,882, Apr. 20, 1988, abandoned.

[30] Foreign Application Priority Data

Apr. 28, 1987 [JP] Japan ............................... 62-103228
Sep. 9, 1987 [JP] Japan ............................... 62-224083

[51] Int. Cl.$^5$ ............................................. C08G 63/06
[52] U.S. Cl. .................................... 528/361; 435/135; 528/354
[58] Field of Search ........................................ 528/361

[56] References Cited

FOREIGN PATENT DOCUMENTS 52,459 5/1982 European Pat. Off. .

PUBLICATIONS

Marchessault et al., Macromolecules, 1984, 17, pp. 1882–1884, "Physical Properties of Naturally Occurring Polyester".

*Primary Examiner*—John Kight, III
*Assistant Examiner*—Frederick Krass
*Attorney, Agent, or Firm*—Wenderoth, Lind & Ponack

[57] ABSTRACT

A random copolymer comprising less than 50 mole % of D-(−)-3-hydroxybutyrate units and more than 50 mole % of D-(−)-3-hydroxyvalerate units, the percentages being based on the total amount of the two units. A process for producing the random copolymer which comprises (1) cultivating a microorganism having the ability to produce poly(3-hydroxybutyrate) to grow and proliferate the cells of the microorganism, (2) cultivating the cells in the presence of a valeric acid or in the copresence of a valeric acid and an n-butyric acid while limiting the amount of nitrogen or phosphorus to produce and accumulate a random copolymer comprising D-(−)-3-hydroxybutyrate units and D-(−)-3-hydroxyvalerate units within the cells, and thereafter, (3) recovering the copolymer from the cells.

3 Claims, No Drawings

RANDOM COPOLYMER COMPRISING D-(−)-3-HYDROXYBUTYRATE UNITS AND D-(−)-3-HYDROXYVALERATE, AND PROCESS FOR PRODUCTION THEREOF

This application is a continuation of now abandoned application, Ser. No. 07/183,882 filed on Apr. 20, 1988.

This invention relates to a random copolymer and a process for its production. More specifically, it relates to a novel random copolymer comprising D-(−)-3-hydroxybutyrate units (to be sometimes referred to as units B) and D-(−)-3-hydroxyvalerate units (to be sometimes referred to as units V) and having a units V/units B mole ratio of more than 1, and a process for producing a random copolymer comprising the units B and units V.

Poly-3-hydroxybutyrate (to be referred to sometimes as PHB) is a thermoplastic polymer which is accumulated as an energy storage substance within the cells of many microorganisms and shows excellent biodegradability and biocompatibility. Hence, it has aroused interest as "clean" plastics for preserving environments and has long been expected to find application in many fields of utility, for example, as a medical material such as a surgical suture and a fixing material for treatment of bone fracture, and as a material for use in slow-releasing systems for slowly releasing pharmaceuticals and agricultural chemicals. Particularly, as synthetic plastics have recently raised a serious social problem from the standpoint of environmental pollution and recycling of resources, PHB has attracted attention as a biopolymer not dependent on petroleum.

However, since PHB has low impact strength and the cost of its production is high, it has not yet gone into commercial production.

Japanese Laid-Open Patent Publications Nos. 150393/1982 and 220192/1984 propose copolymers comprising units B and units V, and processes for production thereof. The processes for producing PHB disclosed in these patent documents, like conventional processes for producing PHB, involve growing the cells of a microorganism in a first step and cultivating the microorganism while limiting the amount of nitrogen or phosphorus, thereby to produce a copolymer.

Japanese Laid-Open Patent Publication No 150393/1982 states that by using propionic acid and isobutyric acid as a substrate in the second step, a copolymer comprising 99.9 to 50 mole % of B units and 0.1 to 50 mole % of other ester units such as V units. However, this patent document describes a working example in which a copolymer containing at most 33 mole % of V units was obtained, and does not specifically describe a copolymer containing the V units in a larger proportion.

Japanese Laid-Open Patent Publication No. 220192/1984, on the other hand, has a qualitative description that a copolymer comprising at least 40 mole % of B units and units of another ester can be produced when carbon from a cellular substance of the waste cells left after extraction of PHB is used in the second step. This patent document quite fails to describe copolymers indicating specific proportions of the units B and the units V. Furthermore, the process of this patent document is complex, and the type, amount, etc. of the cellular substance formed vary greatly depending upon the cultivation conditions. Hence, the process is unstable and not practical.

It is known that as the proportion of the V units in the copolymer increases from 0 to 33 mole %, the melting temperature (Tm) abruptly decreases from 180° to 85° C. [T. L. Bluhm et al., Macromolecules, 19, 2871–2876 (1986)]This means that industrially, it is difficult to obtain a uniform product.

It is an object of this invention to provide a novel random copolymer comprising D-(−)-3-hydroxybutyrate units and D-(−)-3-hydroxyvalerate in which the proportion of the D-(−)-3-hydroxyvalerate units is preferably more than 50 mole % based on the total amount of these units.

Another object of this invention is to provide a process which can produce the random copolymer of this invention containing the D-(−)-3-hydroxyvalerate units in a proportion of more than 50 mole % based on the total amount of the two units in a yield sufficient for practical application, and in which the content of the D-(−)-3-hydroxyvalerate units can be easily controlled to a range of more than 50 mole % to 95 mole %.

Further objects and advantages of this invention will become apparent from the following description.

According to this invention, these objects and advantages of the invention are achieved by a random copolymer comprising less than 50 mole % of D-(−)-3-hydroxybutyrate units and more than 50 mole % of D-(−)-3-hydroxyvalerate units, the percentages being based on the total amount of the two units.

In the present invention, the units B and the units V in the copolymer are represented by the following formulae.

units B: —OCH(CH$_3$)CH$_2$CO—
units V: —OCH(C$_2$H$_5$)CH$_2$CO—

Preferably, the copolymer of this invention comprises 93 to 5 mole % of the B units and 7 to 95 mole % of the V units based on the total amount of the two units.

Preferably, the copolymer of this invention consists essentially of the units B and the units V.

The copolymer of this invention has an intrinsic viscosity [ζ], measured in a chloroform solution at 30° C., of 0.1 to 10 dl/g, more preferably 1 to 9 dl/g.

According to this invention, the copolymer can be produced by a process which comprises (1) cultivating a microorganism having the ability to produce poly-3-hydroxybutyrate to grow the cells of the microorganism,
(2) cultivating the cells in the presence of a valeric acid while limiting the amount of nitrogen or phosphorus to produce and accumulate a random copolymer comprising D-(−)-3-hydroxybutyrate units and D-(−)-3-hydroxyvalerate units within the cells, and thereafter,
(3) recovering the copolymer from the cells.

Any microorganism which has the ability to produce PHB may be used in the process of this invention. In industrial practice, *Alcaligenes faecalis, Alcaligenes ruhlandii, Alcaligenes latus, Alcaligenes aquamarinus* and *Alcaligenes eutrophus*, for example, are advantageously used.

Specific examples of strains belonging to these microorganism species include *Alcaligenes faecalis* ATCC 8750, *Alcaligenes ruhlandii* ATCC 15749, *Alcaligenes latus* ATCC 29712, *Alcaligenes aquamarinus* ATCC 14400, *Alcaligenes eutrophus* H-16 ATCC 17699, and *Alcaligenes eutrophus* NCIB 11597, NCIB 11598, NCIB 11599 and NCIB 11600 which are mutants of *Alcaligenes eutrophus* H-16. In industrial practice, *Alcaligenes eutro-*

*phus* H-16 ATCC 17699 and *Alcaligenes eutrophus* NCIB 11599 are especially preferred.

The microbiological properties of these microorganisms of the genus Alcaligenes are described, for example, in "BERGEY'S MANUAL OF DETERMINATIVE BACTERIOLOGY: Eighth Edition, The Williams & Wilkins Company, Baltimore". The microbiological properties of *Alcaligenes eutrophus* H-16 are described, for example, in "J. Gen. Microbiol., 115, 185-192 (1979)".

According to this invention, these microorganisms are cultivated in two steps as in conventional processes. In a first step, the microorganisms are cultivated to grow and proliferate the cells mainly, and in a second step, the microorganism cells are cultivated while limiting the amount of nitrogen or phosphorus in the cultivation system to form and accumulate the copolymer in the cells.

The first-step cultivation may be carried out by an ordinary cultivation method for growing and proliferating microorganisms using a medium and cultivation conditions suitable for growing and proliferating the microorganisms.

The components of the culture medium may be any substances which the selected microorganism can utilize. In industrial practice, suitable carbon sources include synthetic carbon sources such as methanol, ethanol and acetic acid, inorganic carbon sources such as carbon dioxide, naturally occurring materials such as yeast extract, molasses, peptone and meat extract, carbohydrates such as arabinose, glucose, mannose, fructose and galactose, and sugar alcohols such as sorbitol, mannitol and inositol. Suitable nitrogen sources include inorganic nitrogen compounds such as ammonia, ammonium salts and nitrates and organic nitrogen compounds such as urea, corn steep liquor, casein, peptone yeast extract and meat extract. Suitable inorganic materials include calcium salts, magnesium salts, potassium salts, sodium salts, phosphates, manganese salts, zinc salts, iron salts, copper salts, molybdenum salts, cobalt salts, nickel salts, chromium salts, boron compounds and iodine compounds. As required, vitamins may be used.

The cultivation temperature may be, for example, 20° to 40° C., preferably about 25° to 35° C. The pH of the culture medium may be, for example, about 6 to 10, preferably about 6.5 to 9.5. Under these conditions, the microorganism is cultivated aerobically.

When cultivation is carried out under conditions outside the above-mentioned conditions, proliferation of the microorganism becomes relatively poor. But since the proliferation does not stop under the other conditions, it is permissible to cultivate the microorganism under the other conditions.

The cultivation may be carried out batchwise or continuously.

According to the process of this invention, the cells obtained by the cultivation in the first step are cultivated further while restricting the amount of nitrogen and/or phosphorus.

For example, the microorganism cells are separated and recovered by ordinary solid-liquid separation means from the culture broth obtained in the first-step cultivation, and the recovered cells are cultivated in the second step. Alternatively, in the first-step cultivation, nitrogen and/or phosphorus is substantially exhausted, and without separating and recovering the cells from the culture broth, the culture broth per se is subjected to cultivation in the second step.

The second-step cultivation is the same as the first-step cultivation except that nitrogen and/or phosphorus is substantially exhausted in the culture medium or the culture broth and a valeric acid is included as a carbon source.

The valeric acid is preferably a compound which is an acid represented by the following formula

$CH_2XCHYCH_2CH_2COOH$ wherein X represents a hydrogen atom, a halogen atom or a hydroxyl group, and Y represents a hydrogen atom, a halogen atom, a hydroxyl group or an alkyl group, preferably a methyl group, or its salt.

Examples of the valeric acid are valeric acid, 4-chlorovaleric acid, 4-hydroxyvaleric acid, 4-methylvaleric acid, 4-ethylvaleric acid, 5-hydroxyvaleric acid and 5-chlorovaleric acid. Examples of its salt are sodium and potassium salts of the above acids.

The valeric acid is included in the culture medium used in the second-step cultivation or the culture broth in the second-step cultivation In the latter case, it may be added at any stage of cultivation from its start to end. Preferably, it is included at the initial stage of the cultivation.

The amount of the valeric acid used may be one which is sufficient to produce the copolymer without inhibiting the growth and proliferation of the microorganism, and may be varied with the type of the microorganism strain used and the ratio of the units V to the units B in the copolymer. Generally, as the concentration of the valeric acid in the culture medium or the culture broth is increased, the proportion of the units V in the copolymer increases. For example, to adjust the proportion of the units V in the copolymer to more than 50 mole %, the concentration of the valeric acid in the culture medium and the culture broth is usually about 5 to 40 g, preferably 10 to 30 g, as valeric acid per liter of the culture medium or the culture broth.

In the second-step cultivation, the valeric acid may be used as a sole carbon source. It is possible however to use together another carbon source which the selected microorganism can utilize, such as glucose, fructose, methanol, ethanol, acetic acid, propionic acid, n-butyric acid or lactic acid. If glucose is used as the other carbon source, its concentration should be adjusted to not more than about 1.5 g/l.

According to this invention, the second-step cultivation is preferably carried out in the copresence of a valeric acid and an n-butyric acid. The valeric acid is preferably the compound represented by the above formula or its salt.

The n-butyric acid is preferably a compound which is an acid of the following formula

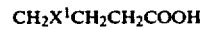
$CH_2X^1CH_2CH_2COOH$ wherein $X^1$ represents a hydrogen atom, a halogen atom or a hydroxyl group, or its salt.

Examples of the n-butyric acid are n-butyric acid, 4-chloro-n-butyric acid and 4-hydroxy-n-butyric acid. Examples of its salt are sodium and potassium salts of these acids.

The valeric acid and the n-butyric acid are included in the culture medium used in the second-step cultivation or the culture broth in the second-step cultivation.

In the latter case, they may be included at any stage of the cultivation from its start to end. Preferably, they are added at the initial stage of the cultivation.

The amounts of the valeric acid and the n-butyric acid may be that which is sufficient to form the copolymer without inhibiting the growth and proliferation of the microorganism, and may vary depending upon the type of the microorganism strain used, and the desired mole ratio of the units V to the units B. The total concentration of the valeric acid and the n-butyric acid in the culture medium and the culture broth is usually about 5 to 40 g, preferably to 10 to 30 g, calculated as valeric acid or n-butyric acid per liter of the culture medium or the culture broth.

The molar proportion of the units V in the copolymer can be higher as the proportion of the valeric acid in the culture medium or the culture broth is made higher or the proportion of the n-butyric acid is made lower.

Usually, it is advantageous to limit the n-butyric acid/valeric acid mole ratio to more than 0 to 10, preferably more than 0 to 5.

In the second-step cultivation, the valeric acid and the n-butyric acid may be used as sole carbon sources. They may, however, be used in combination with a small amount of another carbon source which the microorganism can utilize, for example glucose, fructose, methanol, ethanol, acetic acid, propionic acid and lactic acid. However, if glucose is used as the other carbon source, its concentration should be adjusted to not more than about 1.5 g/liter.

According to this invention, the cells are separated and recovered from the resulting culture broth by ordinary solid-liquid separating means such as filtration and centrifugation. The cells are then washed and dried to obtain dry cells. The resulting copolymer is extracted from the dry cells in a customary manner, for example by using an organic solvent such as chloroform.

By the process of this invention, the ratio of the units V to the units B can be freely adjusted, and a copolymer having a major proportion of the units V and a minor proportion the units B can be obtained.

Because of these excellent properties, the copolymers obtained by this invention are expected to find many applications, for example as medical materials such as surgical sutures and fixing materials in the treatment of bone fracture, and in slow-releasing systems.

Those copolymers of this invention which contain a major proportion of the units V have a lowered melting temperature, high stability at the melting temperature and low crystallinity. Hence, they can be spun, rolled, or otherwise molded easily and stably to give fibers or films having high strength, pliability and toughness.

The following examples illustrate the present invention more specifically.

EXAMPLE 1

A copolymer was produced using *Alcaligenes eutrophus* NCIB 11599.

First-step cultivation

The above microorganism was cultivated at 30° C. for 24 hours in a culture medium having the following composition. The cells were separated from the culture broth in the final phase of the logarithmic growth stage.

| Composition of the culture medium: | |
| --- | --- |
| Yeast extract | 10 g |
| Polypeptone | 10 g |
| Meat extract | 5 g |
| $(NH_4)_2SO_4$ | 5 g |

These ingredients were dissolved in 1 liter of deionized water and its pH was adjusted to 7.0.

Second-step cultivation

The cells obtained by the first-step cultivation were suspended in an amount of 5 g per liter in a culture medium having the following composition, and cultivated at 30° C. for 48 hours. The cells were separated by centrifugation from the resulting culture broth.

| Composition of the culture medium: | |
| --- | --- |
| 0.5 M aqueous potassium hydrogen phosphate solution | 39.0 ml |
| 0.5 M aqueous dipotassium hydrogen phosphate solution | 53.6 ml |
| 20 wt/v % aqueous magnesium sulfate solution | 1.0 ml |
| Carbon source (*) | |
| Mineral solution (**) | 1.0 ml |

The above ingredients were dissolved in 1 liter of deionized water and its pH was adjusted to 7.0.

(*) Valeic acid and/or glucose (g/liter-medium) was used in the following proportions as the carbon source.

| | Valeic acid | Glucose |
| --- | --- | --- |
| (1) | 20 | 0 |
| (2) | 20 | 0.5 |
| (3) | 20 | 1.0 |
| (4) | 0 | 20 |

| (**) Composition of the mineral solution | |
| --- | --- |
| $CoCl_2$ | 119.0 mg |
| $FeCl_3$ | 9.7 g |
| $CaCl_2$ | 7.8 g |
| $NiCl_2$ | 118.0 mg |
| $CrCl_2$ | 62.2 mg |
| $CaSO_4$ | 156.4 mg |

The ingredients were dissolved in 1 liter of 0.1N-HCl.

Treatment of the Cells

The cells obtained by the second-step cultivation were washed with distilled water and subsequently washed with acetone. The washed cells were dried at 20° C. under a pressure of 0.1 mm Hg. There was no substantial difference in the weight of dry cells among the uses of (1), (2), (3) and (4).

Separation and recovery of the copolymer

The copolymer was extracted with hot chloroform from the resulting dry cells. Hexane was added to the extract to precipitate the copolymer. The precipitate was collected by filtration and dried to recover the copolymer.

Characteristics of the copolymer

The composition, intrinsic viscosity, melting temperature, and the heat of fusion of the resulting copolymer were measured by the following methods.

Composition: 500 MHz, $^1$H—NMR spectrum

Intrinsic viscosity [ζ]: in chloroform at 30° C.

Melting temperature Tm: DSC measurement (temperature elevation rate 10° C./min.)

Heat of fusion ΔH: DSC measurement The results are shown in Table 1.

The sequence distribution of the copolymer obtained when (1) was used was determined from 125 MHz $^{13}$C NMR spectrum.

Specifically, by the method of the present inventor and others Y. Doi et al., "Macromolecules", 19, 2860–2864 (1986)], the dyad sequence distribution of the units B and units V was determined from the multiplet resonance structure of carbonyl carbon. This copolymer was found to have the following sequence distribution.

| | |
|---|---|
| BB (butyrate-butyrate) dyad fraction | 3% |
| BV (butyrate-valerate) and VB (valerate-butyrate) dyad fractions | 12% |
| VV (valerate-valerate) dyad fraction | 85% |

This sequence distribution shows that the copolymer has a random sequence distribution of monomeric units B and V.

EXAMPLE 2

Example 1 was repeated except that *Alcaligenes eurotophus* H-16 ATCC 17699 was used, and valeric acid was used as the carbon source in an amount of 20 g/liter-culture medium. The results are shown in Table 1.

| | Valeric acid (g/l) | n-Butyric acid (g/l) |
|---|---|---|
| (1) | 18 | 2 |
| (2) | 16 | 4 |
| (3) | 14 | 6 |
| (4) | 12 | 8 |
| (5) | 10 | 10 |
| (6) | 5 | 15 |

In the same way as in Example 1, the resulting cells were treated and the copolymer was separated and recovered from the dry cells. The properties of the copolymers were examined. The weight of the dry cells and the properties of the copolymers are shown in Table 2.

The copolymer obtained when (3) was used as the carbon source was found to have the following sequence distribution.

| | |
|---|---|
| BB (butyrate-butyrate) dyad fraction | 32% |
| BV (butyrate-valerate) and VB (valerate-butyrate) dyad fractions | 48% |
| VV (valerate-valerate) dyad fraction | 20% |

This sequence distribution shows that the copolymer has a random copolymer sequence distribution.

| Carbon sources | Weight of dry cells (g) | Content of the copolymer in the dry cells (wt. %) | Composition (mole %) | | Intrinsic viscosity (dl/g) | Melting temperature (°C.) | Heat of fusion (cal/g) |
|---|---|---|---|---|---|---|---|
| | | | Units B | Units V | | | |
| (1) | 5.8 | 43 | 40 | 60 | 3.9 | 105 | 7.2 |
| (2) | 6.0 | 47 | 44 | 56 | 4.2 | 100 | 6.5 |
| (3) | 5.9 | 48 | 55 | 45 | 4.1 | 83 | 4.5 |
| (4) | 5.8 | 37 | 70 | 30 | 3.5 | 68,159 | — |
| (5) | 6.8 | 46 | 74 | 26 | 4.0 | 70,163 | — |
| (6) | 7.6 | 55 | 85 | 15 | 4.4 | 152 | 8.5 |

| Example | Content of the copolymer in dry cells (wt. %) | Composition (mole %) | | Intrinsic viscosity (dl/g) | Weight average molecular weight ($\times 10^5$) | Melting temperature (°C.) | Heat of fusion (cal/g) |
|---|---|---|---|---|---|---|---|
| | | Units B | Units V | | | | |
| 1 | | | | | | | |
| (1) | 36 | 10 | 90 | 4.0 | 5.7 | 108 | 13.8 |
| (2) | 24 | 27 | 73 | 2.7 | 3.5 | 106 | 9.9 |
| (3) | 17 | 39 | 61 | 2.0 | 2.4 | 104 | 6.9 |
| (4) | 54 | 100 | 0 | 4.4 | 6.4 | 178 | 21.7 |
| 2 | 38 | 34 | 66 | 2.0 | 2.4 | 104 | 8.4 |

EXAMPLE 3

*Alcaligenes europhus* NCIB 11599 was cultivated in the same way as in Example 1 except that valeric acid and n-butyric acid in the following proportions were used in combination as the carbon source.

What we claim:

1. A random copolymer comprising 5 to 39 mole % of D-(−)-3-hydroxybutyrate units and 95 to 61 mole % of D-(−)-3-hydroxyvalerate units, the mole percentages being based on the total amount of the two units.

2. The random copolymer of claim 1 which consists essentially of D-(−)-3-hydroxybutyrate units and D-(−)-3-hydroxyvalerate units.

3. The random copolymer of claim 1 which has an intrinsic viscosity [ζ], measured in a chloroform solution at 30° C., of 0.1 to 10 dl/g.

* * * * *